United States Patent
Rubini et al.

(10) Patent No.: US 6,593,269 B1
(45) Date of Patent: Jul. 15, 2003

(54) CATALYSTS FOR EXOTHERMIC REACTIONS ON A FIXED BED

(75) Inventors: Carlo Rubini, San Fermo Della Battaglia (IT); Marinella Malentacchi, Castiglion Fiorentino (IT)

(73) Assignee: Sud Chemie MT S.R.L., Milan (IT)

( * ) Notice: Subject to any disclaimer, the term of this patent is extended or adjusted under 35 U.S.C. 154(b) by 0 days.

(21) Appl. No.: 09/476,547

(22) Filed: Jan. 3, 2000

(30) Foreign Application Priority Data

Jan. 8, 1999 (IT) .......................... MI99A0016

(51) Int. Cl.[7] .................... B01J 27/122; B01J 27/06; B01J 27/138; B01J 27/125; C07C 19/00
(52) U.S. Cl. .................... 502/225; 502/224; 502/226; 502/229; 502/231; 502/337; 502/343; 502/355; 570/245
(58) Field of Search .................... 502/345, 225, 502/343, 226, 355, 229, 337, 231, 300, 224, 527, 341, 342; 423/659; 570/224, 245

(56) References Cited

U.S. PATENT DOCUMENTS

| | | | | |
|---|---|---|---|---|
| 3,720,723 A | * | 3/1973 | Pritchett | 260/658 R |
| 4,025,461 A | * | 5/1977 | Croce et al. | 252/462 |
| 4,366,093 A | * | 12/1982 | Shiozaki et al. | 252/477 R |
| 4,753,914 A | * | 6/1988 | Eichhorn et al. | 502/225 |
| 5,053,567 A | * | 10/1991 | Correia et al. | 570/243 |
| 5,080,872 A | | 1/1992 | Jezl et al. | 422/201 |
| 5,113,027 A | * | 5/1992 | Mainz et al. | 570/224 |
| 5,116,799 A | * | 5/1992 | Correia et al. | 502/225 |
| 5,202,511 A | * | 4/1993 | Salinas, III et al. | 570/245 |
| 5,243,111 A | * | 9/1993 | Petit et al. | 570/243 |
| 5,371,403 A | | 12/1994 | Huang et al. | 257/691 |
| 5,635,438 A | * | 6/1997 | Cowfer et al. | 502/319 |
| 5,736,076 A | | 4/1998 | Meissner et al. | 264/29.6 |
| 5,972,827 A | * | 10/1999 | Petit et al. | 502/225 |

FOREIGN PATENT DOCUMENTS

| | | | |
|---|---|---|---|
| DE | 197 18 871 | 11/1998 | |
| EP | 0060317 | * 9/1982 | ............ B01J/37/04 |
| EP | 0732146 A1 | * 9/1996 | ............ B01J/35/10 |
| EP | 0775522 A1 | * 5/1997 | ............ B01J/35/02 |
| EP | 0794004 A1 | * 9/1997 | ............ B01J/23/83 |
| EP | 0879641 A1 | * 5/1998 | ............ B01J/23/44 |
| GB | 997 601 | 7/1965 | |
| GB | 1 547 288 | 6/1979 | |

* cited by examiner

Primary Examiner—Wayne A. Langel
Assistant Examiner—Jonas N. Strickland
(74) Attorney, Agent, or Firm—Welsh & Katz, Ltd.

(57) ABSTRACT

Catalysts for exothermic reactions conducted in a fixed bed, comprising an inert diluent constituted by metal granules in which the metal has a thermal conductivity of more than 0.5 W/cm/K, particularly catalysts for the oxychlorination of ethylene to 1,2-dichloroethane.

8 Claims, 1 Drawing Sheet

CATALYSTS FOR EXOTHERMIC REACTIONS ON A FIXED BED

Figure 1:
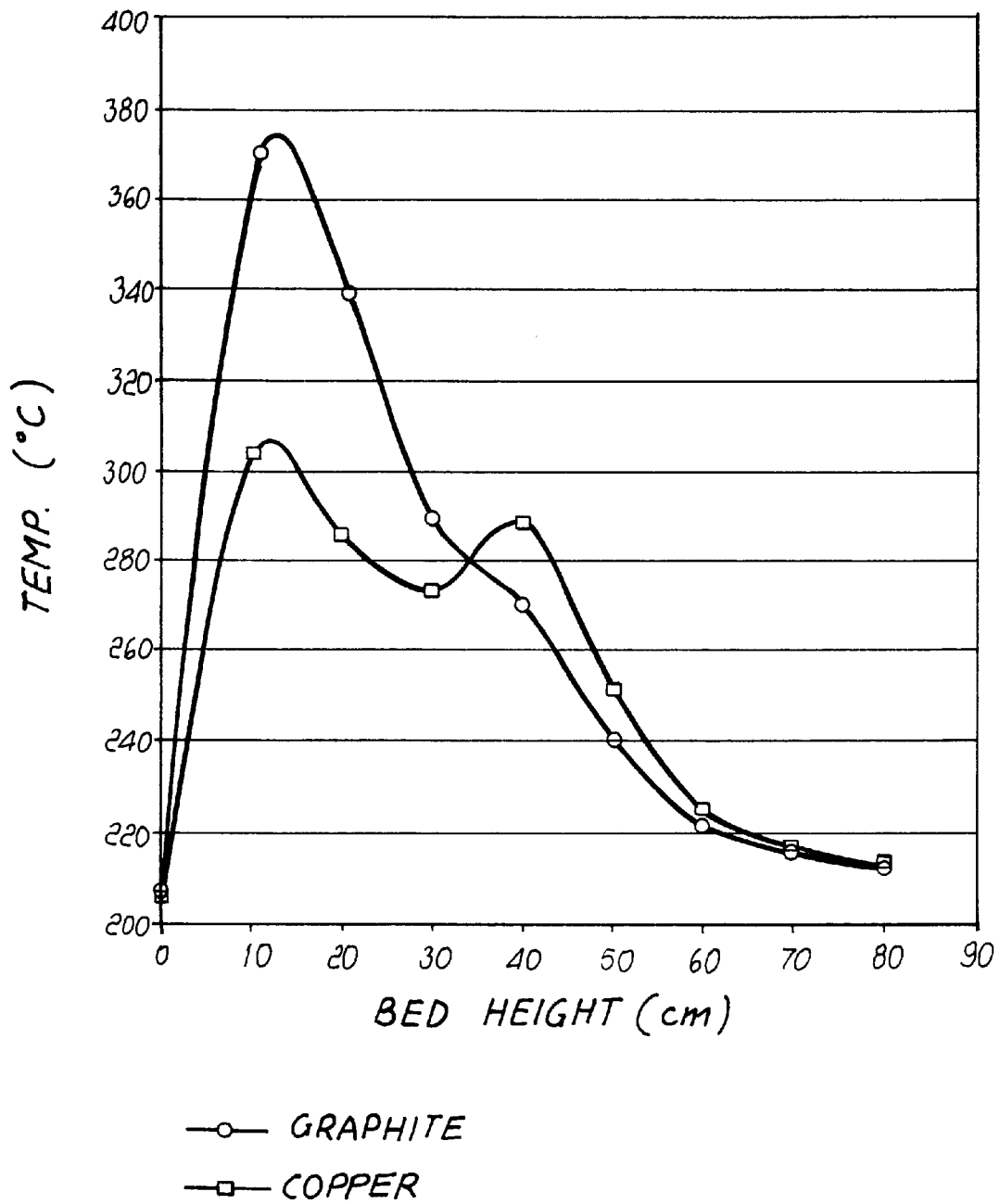

The present invention relates to compositions comprising a catalyst for exothermic reactions conducted on a fixed bed and to a metal diluent used to reduce or eliminate the formation of hot spots in the fixed bed.

In particular, it relates to compositions in which the catalyst is a catalyst for the oxychlorination of ethylene to 1,2-dichloroethane.

BACKGROUND OF THE INVENTION

Removal of the reaction heat in exothermic reactions by the cooling fluid is decisive for reaction control and therefore for the possibility to achieve high conversions and selectivities.

Whereas in fluid-bed operations this problem is scarcely important due to the high overall exchange coefficient that can be achieved in these conditions, in the fixed-bed technology the problem of removing heat is extremely important, since at the inlet of the bed the concentration of the reagents is high and therefore the reaction rate and the production of heat are the highest. The temperature inside the catalytic bed therefore tends to rise rapidly, creating regions of high temperature (hot spots) which produce considerable problems in terms of rapid aging of the catalyst and cause a consequent loss of selectivity due to the increase in secondary reactions. Bearing in mind that the amount of heat exchanged is governed, for a given cooling surface and for a given overall exchange coefficient, by the difference between the temperature inside the bed and the temperature of the cooling fluid, and that in normal conditions the rate of heat exchange is regulated by said temperature difference, the temperature in the hot spot will tend to rise until the difference in temperature removes all the heat produced by the reaction.

In the final part of the bed, instead, the reaction rate (and therefore the production of heat) is very low and hot spots accordingly do not occur.

In order to reduce the hot spot temperature by acting on the catalyst one can use two approaches:

using a scarcely active catalyst in the region of the catalytic bed at the inlet of the reagents;

diluting the catalyst in said region by using inert solid diluents.

The diluents used so far comprise materials such as graphite, silicon carbide, macroporous carbon, low surface area alumina, silica and glass beads.

These diluents, due to their low thermal conductivity coefficient, are not suitable to effectively transfer heat from the hot spot region to the wall of the heat exchanger.

Furthermore, again due to their low thermal conductivity, the diluents are unable to adequately transfer heat from the regions where, due to uneven mixing of the catalyst and of the diluent, peaks in the concentration of the catalyst occur, with consequent forming of hot spots.

SUMMARY OF THE INVENTION

It has now been unexpectedly found that the use as diluent of metals which are inert toward the reagents and the reaction products and having high thermal conductivity allows not only to improve the yield and selectivity of the catalyst and therefore the productivity of the plant but also to reduce or avoid the loss and/or aging of the catalyst in cases in which these problems tend to occur.

In particular, in the case of the oxychlorination of ethylene to 1,2-dichloroethane, diluents with high thermal conductivity allow to provide the reaction in a single stage instead of in multiple stages as normally occurs.

The diluents that can be used in the compositions according to the invention are metals with a thermal conductivity of more than 0.5 W/cm/K (value considered in the temperature range from 400K to 1573K, equal to 127° to 1000° C).

DESCRIPTION OF THE INVENTION

Copper has a thermal conductivity (W/cm/K) of 3.93 at 400K and 3.39 at 1573K; the values for aluminum is 2.4 at 400K and 2.18 at 800K; the values for nickel are 0.8 and 0.76 at 400K and at 1200K respectively; zinc has a conductivity of more than 1 in the temperature range being considered.

The following are examples of coefficients related to materials not included among the usable ones: 0.13 W/cm/K at 673K for alumina: 0.04 and 0.01 for graphite at 400K and 1200K; 0.19 and 0.25 for stainless steel at 573K and 973K.

The metals usable in the compositions according to the invention are chosen so as to be substantially inert with respect to the reagents and to the products of the reaction in which they are used.

Copper is the preferred metal, due to its high thermal conductivity and high density which allows to provide high heat capacity per unit volume of metal and therefore to absorb and then rapidly transfer considerable amounts of heat.

Aluminum and nickel, too, are conveniently usable, particularly in reaction conditions in which high chemical inertness is required.

The metallic diluents are preferably used with a geometric shape and dimensions which are similar to those of the granular catalyst with which they are mixed. It is also possible to use different shapes and dimensions.

Preferred shapes are those that provide a wide surface area per unit volume of diluent associated with significant void percentages. This is done in order to facilitate heat exchange and reduce pressure losses.

Examples of these shapes are the cylindrical ones with a through bore having a wide diameter and annular shapes.

Examples of cylindrical shapes are multilobed shapes with through bores at the various lobes and other shapes with a large geometric area.

Shapes of this type (described for catalysts and carriers) are reported in U.S. Pat. No. 5,330,958, whose description is included herein by reference.

The dimensions of the cylindrical shapes are generally between 3 and 10 mm in height and 5–10 mm in diameter.

The percentage of diluent is a function of the exothermic nature of the reaction and of its kinetics.

Percentages from 10 to 80% by volume on the mixture can be used conveniently.

The catalytic compositions that contain the metal diluent are used so as to form the bed in the part at the inlet of the reagents.

It is also possible to use various bed layers in which the concentration of the catalyst rises toward the lower part of the bed.

A typical example of exothermic reaction conducted on a fixed bed in which the compositions according to the invention can be used conveniently is the oxychlorination of ethylene to 1,2-dichloroethane.

Examples of other reactions are: oxidation of n-butane to maleic anhydride; oxidation of o-xylene or naphthalene to phthalic anhydride; synthetic natural gas from methane; vinyl acetate from ethylene and acetic acid; ethylene oxide from ethylene.

As mentioned, in the case of the oxychlorination reaction it has been found that, in addition to the advantage of higher yields and selectivities, the use of diluted catalysts according to the invention allows to conduct the reaction in a single stage instead of multiple stages, as normally occurs in the processes of the prior art.

The diluted catalysts according to the invention are used under the reaction conditions that are used normally; however, it is possible to optimize said conditions in order to utilize the higher performance of the catalysts in the best possible manner, in terms of both yield and selectivity.

Catalysts that can be diluted with the metal diluents comprise all the catalysts that can be used in exothermic reactions conducted on a fixed bed.

In the case of the catalysts for the oxychlorination of ethylene to 1,2-dichloroethane, the representative and preferred usable catalysts are based on cupric chloride or cuprous hydroxychloride, comprising promoters chosen among chlorides of alkal metals and/or chlorides of alkaline-earth metals, optionally of rare earths.

These catalysts are supported on inert porous supports, particularly alumina with a surface area between 50 and 300 $m^2/g$.

Catalysts of this type are amply described in the literature and in particular in EP-A-176432, the description of which is included herein by reference. In the catalysts described in EP-A-176432, the concentration of cupric chloride is lower on the surface than inside the catalyst granule.

The following examples are provided to illustrate but not to limit the scope of the invention.

EXAMPLES

A) Preparation of the Catalyst 300 g of alumina, pelletized in the form of three-lobed cylindrical granules having three equidistant through bores which are parallel to the axis of the cylinder, were heated to 450° C. They were then impregnated with an aqueous solution containing 9.33 g of CsCl and heated to 500° C. for is 1 h.

An aqueous solution containing 58.33 g of $CuCl_2.2H_2O$ and 12.45 g of KCl (so as to obtain a Cu content of 4% and a K content of 2%, expressed as percentage by weight on the final catalyst) was prepared separately. In order to facilitate dissolution of the chlorides, 8 g of HCl in a 35% aqueous solution were added. This solution was used to impregnate the support pellets pre-treated with CsCl.

The resulting catalyst was stove-dried at 120° C. for one night and was ready for use.

B) Description of the Reactor

In order to check the performance of the catalysts, diluted with different materials, a tubular reactor having an inside diameter of 26 mm and a height of 130 cm was used. The construction material of the reactor was Ni 200. The reactor was provided with a thermostatic-control jacket in which oil circulated and with ducts for feeding the reagents.

The reagents (HCl, $C_2H_4$, $O_2$ and $N_2$) were metered and controlled by means of mass flow meters.

At the outlet of the reactor, the reaction products were cooled: the liquid products (EDC, unconverted HCl, chlorinated byproducts and reaction water) were collected in a flask, whereas the non-condensables ($O_2$, $N_2$, CO and $CO_2$) were sent to the stack after being measured and analyzed by chromatography. The liquid products were composed of two phases, an aqueous one and an organic one; the two phases were separated in a separator funnel, weighed and analyzed: titration of the hydrochloric acid was performed for the aqueous phase, whereas the organic phase was analyzed by chromatography in order to determine the purity of the EDC.

The reagents were normally fed at the temperature of 210° C.; the reaction was brought to the chosen temperature and when steady and constant conditions were reached, liquid products collection and gas monitoring was performed for a period of 1–2 hours.

Comparison Example 1

The catalyst prepared as described above was loaded into the reactor. It was mixed with graphite as follows:

a layer of undiluted catalyst with a thickness of 50 cm was loaded into the lower part of the reactor (the part near the product outlet); the amount loaded was 185.2 g (equal to 270 cc);

catalyst (45.5 g, equal to 64 cc) mixed with graphite (82.2 g, equal to 96 cc) was loaded into the upper part of the reactor, for a height of 30 cm; the resulting mixture contained 40% of catalyst by volume.

The total height of the catalytic bed was therefore 80 cm. A thermocouple supporting sheath was arranged coaxially in the reactor; 9 thermocouples for detecting the temperature of the reactor were inserted in said sheath at a distance of 10 cm each. By means of the various thermocouples it was possible to obtain the thermal profile of the reactor; said profile is plotted in the chart of the Figure.

Samples were taken in order to determine the performance: the conditions of the test and the associated results are listed in Table 1.

Example 1

The same method as in comparison example 1 was used. The amounts of catalyst are the same; the only difference is the type of diluent used, which is in the form of copper rings which are 7 mm high, 6 mm in outside diameter and 5.6 mm in inside diameter. The amount of diluent by weight is 225.7 g (96 cc).

The results of the tests are given in table 1; the chart of the Figure also plots for comparison the thermal profile obtained in example 1.

The influence of the use of copper as diluent on the performance is evident; due to a lower hot spot, a significant increase in activity (expressed by the conversion of the hydrochloric acid) and in selectivity (due to reduced formation of carbon oxides and chlorinated byproducts) is achieved.

The disclosures in Italian Patent Application No. MI99A000016 from which this application claims priority are incorporated herein by reference.

TABLE 1

| CONSTANT CONDITIONS | | | |
|---|---|---|---|
| Bed height | cm | 80 | |
| Through put (tot) | Nl/h | 720 | |
| Pressure | Ate | 3 | |
| Oil temp. | ° C. | 210 | |
| Linear velocity | cm/s | 18.5 | |
| Contact time | Sec. | 4.3 | |

| | Molar ratio | Molar ratio | Hot spot Temperature | Conversion % | | Selectivity % mol | | | EDC Purity |
|---|---|---|---|---|---|---|---|---|---|
| | Cl/C | $O_2/C_2H_4$ | ° C. | HCl | $C_2H_4$ | EDC | COX | EC | % molar |
| Comparison | 0.393 | 0.187 | 370 | 86.2 | 34.6 | 95.8 | 2.40 | 0.12 | 97.9 |
| Example | 0.424 | 0.201 | 370 | 85.2 | 36.9 | 94.6 | 2.39 | 0.26 | 98.7 |
| Example 1 | 0.401 | 0.193 | 304 | 89.8 | 36.5 | 98.7 | 1.25 | 0.02 | 99.9 |
| | 0.425 | 0.202 | 305 | 89.3 | 38.4 | 98.0 | 1.25 | 0.16 | 99.3 |
| | 0.430 | 0.207 | 305 | 90.3 | 39.3 | 96.0 | 1.31 | 0.16 | 99.3 |

Note:
EDC: 1,2 dichloroethane
EC : ethyl chloride

What is claimed is:

1. Oxychlorination catalytic compositions comprising a catalyst in the form of granules suitable for exothermic reactions conducted on a fixed bed, and an elemental metal diluent having a metal selected from the group consisting of aluminum, zinc and nickel and, wherein the metal of the diluent has thermal conductivity values of more than 0.4W/cm/K in the range from 400 K to 1573 K.

2. Compositions according to claim 1, wherein the metal diluent is in the form of cylindrical granules having at least one through bore or annular granules.

3. Compositions according to claim 2, wherein the cylindrical granule has a multilobed configuration with through bores at the lobes.

4. Compositions according to claim 1, wherein the diluent is used in an amount of 10 to 80% by volume on the volume of the composition.

5. Compositions according to claim 1, wherein the catalyst is for the oxychlorination of ethylene to 1,2-dichloroethane.

6. Compositions according to claim 5, wherein the catalyst comprises a copper compound supported on an inert porous support medium.

7. Composition according to claim 6, wherein the catalyst comprise a copper compound select from the group consisting of cupric chloride and copper hydroxychloride supported on alumina having a surface area from 50 to 300 $m^2/g$.

8. An oxychlorination compositions according to claim 7, wherein the catalyst comprises a promoter selected from the group consisting of chlorides of alkali metals and chlorides of alkaline-earth metals optionally in mixture with chlorides of rare earth metals.

* * * * *